US008747383B2

(12) United States Patent
Francis et al.

(10) Patent No.: US 8,747,383 B2
(45) Date of Patent: Jun. 10, 2014

(54) PROCESS AND SYSTEM FOR IONTOPHORETIC WRINKLE REDUCTION

(75) Inventors: Ray Francis, Irvine, CA (US); John Trengove, Irvine, CA (US); Greg Hunt, Irvine, CA (US); Josh Hoyt, Portland, OR (US); Jim Thorne, Portland, OR (US); Darrick Carter, Seattle, WA (US)

(73) Assignee: University Medical Pharmaceuticals Corp., Irvine, CA (US)

( * ) Notice: Subject to any disclaimer, the term of this patent is extended or adjusted under 35 U.S.C. 154(b) by 466 days.

(21) Appl. No.: 12/970,224

(22) Filed: Dec. 16, 2010

(65) Prior Publication Data

US 2011/0190724 A1 Aug. 4, 2011

Related U.S. Application Data

(60) Provisional application No. 61/288,088, filed on Dec. 18, 2009.

(51) Int. Cl.
*A61M 31/00* (2006.01)
(52) U.S. Cl.
USPC ............................................ 604/501; 604/20
(58) Field of Classification Search
USPC ..................................................... 604/20, 501
See application file for complete search history.

(56) References Cited

U.S. PATENT DOCUMENTS

| 4,372,296 | A | | 2/1983 | Fahim |
| 4,406,658 | A | * | 9/1983 | Lattin et al. ..................... 604/20 |
| 4,979,938 | A | | 12/1990 | Stephen et al. |
| 6,175,763 | B1 | * | 1/2001 | Sorenson et al. ............... 604/20 |
| 6,823,202 | B2 | * | 11/2004 | Hause, Jr. ...................... 600/347 |
| 6,866,856 | B2 | | 3/2005 | Lu et al. |
| 7,427,273 | B2 | | 9/2008 | Mitsui |
| 7,479,133 | B2 | | 1/2009 | Sun et al. |
| 2004/0167461 | A1 | * | 8/2004 | Nitzan et al. ..................... 604/20 |
| 2004/0267189 | A1 | | 12/2004 | Mavor |
| 2005/0015042 | A1 | * | 1/2005 | Sun et al. ........................ 604/20 |

(Continued)

FOREIGN PATENT DOCUMENTS

| JP | 09169617 | 6/1997 |
| KR | 20-0327534 | 9/2003 |
| KR | 20-0403033 | 12/2005 |
| WO | WO 96/36394 | 11/1996 |

OTHER PUBLICATIONS

Extended European Search Report re App No. PCT/US2010061029 dated Jun. 28, 2013 in 6 pages.
International Search Report dated Aug. 31, 2011 PCT/US2010/061029 in 4 pages.

*Primary Examiner* — Kevin C. Sirmons
*Assistant Examiner* — Edelmira Bosques
(74) *Attorney, Agent, or Firm* — Knobbe, Martens, Olson & Bear LLP (57) ABSTRACT

A method and system for wrinkle reduction. The method includes the steps of positioning and applying a patch to skin of a consumer and adhesively securing the patch to the skin. A chemical composition on the patch includes both active ingredients and adhesive. A pair of electrodes are connected to a battery-driven, microprocessor-based controller. A current is applied through the electrodes in the patch for a selected time. The chemical composition in the patch is propelled into the consumer through use of the current in order to relax the skin of the consumer. The patch is removed and any residue of the chemical composition is massaged into the skin.

14 Claims, 7 Drawing Sheets

(56) References Cited

U.S. PATENT DOCUMENTS

| | | |
|---|---|---|
| 2006/0100567 A1* | 5/2006 | Marchitto et al. .............. 604/19 |
| 2006/0167403 A1* | 7/2006 | Henley et al. .................. 604/20 |
| 2007/0276451 A1 | 11/2007 | Rigaux |
| 2009/0048556 A1 | 2/2009 | Durand |
| 2009/0149800 A1 | 6/2009 | Durand |
| 2009/0299267 A1 | 12/2009 | Durand |
| 2010/0286590 A1 | 11/2010 | Durand |

* cited by examiner

PROCESS AND SYSTEM FOR IONTOPHORETIC WRINKLE REDUCTION

CROSS-REFERENCE

This application claims priority to U.S. Provisional Patent Application Ser. No. 61/288,088, filed Dec. 18, 2010, incorporated in its entirety herein by reference.

BACKGROUND OF THE INVENTION

1. Field of the Invention

The present invention relates and is directed to a process or method of use and a system including a disposable patch to treat wrinkles and line lines with a chemical composition administered by iontophoresis.

2. Prior Art

There are various known procedures and various known chemical compositions for treating, reducing or preventing fine lines or wrinkles of the facial skin. It is known that moisturizers containing amino acids play a significant role in skin care by increasing skin elasticity and smoothing the skin. In addition, anti-aging active agents are known to change the skin condition by smoothing and tightening.

Chemical compositions may be administered topically, such as lotions, or administered through transdermal patches. Additionally, chemical compositions may be administered by direct injection. Chemical compositions presently available include those which moisturize the outer skin or epidermis. Other compositions tend to promote cell growth in the skin. Other treatments of wrinkles and line lines include botulinum toxin (marketed under the trademark Botox®) which inhibits neurotransmission in nerve cells, thereby causing contracted muscles to relax.

In order to increase the speed and effectiveness of delivery of chemical compositions for treatment, it is known to utilize sonic vibrations. For example, Fahim (U.S. Pat. No. 4,372,296) discloses topical treatment of acne with zinc salt and ascorbic acid in a pharmaceutical carrier which is applied with ultra sonic vibrations.

Stephen et al. (U.S. Pat. No. 4,979,938) disclose a method of treating acne using an applicator electrode having a solution capable of producing hydroxyl ions. An applicator electrode is placed against the skin and a voltage differential is applied to produce and drive hydroxyl ions into the skin tissue.

Sun et al. (U.S. Pat. No. 7,479,133) discloses a device for treating acne or rosacea by applying an electrical charge with two conductive electrodes in communication with a carrier containing an electrolyte.

More recently, the Durand patent publications (U.S. Patent Publication No. 2009/0048556 and 2009/0149800) disclose a drug delivery system including a pair of electrodes coupled to drug reservoirs 24 controlled by a microprocessor 12. The microprocessor may be programmed through a wireless signal receiver.

Notwithstanding the forgoing, there remains a need for an effective, simple, non-invasive and non-surgical process and system utilizing a disposable patch for treating wrinkles and fine lines.

There also remains a need for a process and system utilizing a disposable patch for wrinkle reduction which may be manufactured at low-cost and high volume.

There also remains a need for a process and system utilizing a disposable patch for wrinkle reduction with precision timing of delivery of active ingredients.

There also remains a need for an apparatus having an adhesive disposable patch with a plurality of active ingredients, a power supply, and a controller in communication with the power supply controlling current using a ramping current profile.

SUMMARY OF INVENTION

The present invention is directed to a process or method of use and a system for wrinkle reduction.

The system includes a patch assembly applied and adhesively secured to the skin of the consumer. Each patch assembly includes a substantially planar top sheet and a substantially planar substrate. Connectors or snaps pass through the top sheet and substrate. On the substrate is a layer of a chemical composition including active ingredients and an adhesive in order to adhere to the skin.

The patch assembly or assemblies are connectable to a detachable electronic locket assembly. The locket assembly may include a housing to form an enclosure. Within the enclosure of the housing is a battery which powers a microprocessor based controller or printed circuit board (PCB). The controller is wired to a pair of electrodes through wires to a wiring harness. The housing, the battery and the controller are suspended from the wiring harness.

In order to use the present invention, the patch assembly or assemblies are positioned and aligned on the skin so that the chemical composition is in contact with and applied to the skin. A pair of electrodes are connected to the connectors or snaps of the patch assembly.

A current is applied from the locket assembly through the electrodes into the chemical composition of the patch assembly for a selected time period. In some embodiments, applying a current through said electrodes in said patch includes: ramping up current with an initial polarity until a target current is reached; maintain said target current for a select time period; ramping down current to zero; ramping up current with a reverse polarity until a target current is reached; maintaining said target current for a select period of time; and ramping down said current to zero. The active ingredients of the chemical composition are propelled into the skin of the consumer in order to relax the skin. After a selected period of time, the current is stopped and the patch assembly is removed. The time period can be monitored by a timer which is activated by contact of the patch with the skin.

The patch assembly may then be disconnected from the locket assembly. The patch assembly may thereafter by discarded and the locket assembly may be reused.

BRIEF DESCRIPTION OF THE DRAWINGS

FIG. 3A is a patch assembly of a second preferred embodiment while

DETAILED DESCRIPTION OF THE PREFERRED EMBODIMENTS

The embodiments discussed herein are merely illustrative of specific manners in which to make and use the invention and are not to be interpreted as limiting the scope of the present invention.

While the invention has been described with a certain degree of particularity, it is to be noted that many modifications may be made in the details of the invention's construction and the arrangement of its components without departing from the spirit and scope of this disclosure. It is understood that the invention is not limited to the embodiments set forth herein for purposes of exemplification.

The present invention includes at least two preferred embodiments—a first preferred embodiment utilized on the skin surrounding the eyes of a consumer and a second preferred embodiment utilized on the forehead and bridge of the nose of a consumer.

Figure 1:
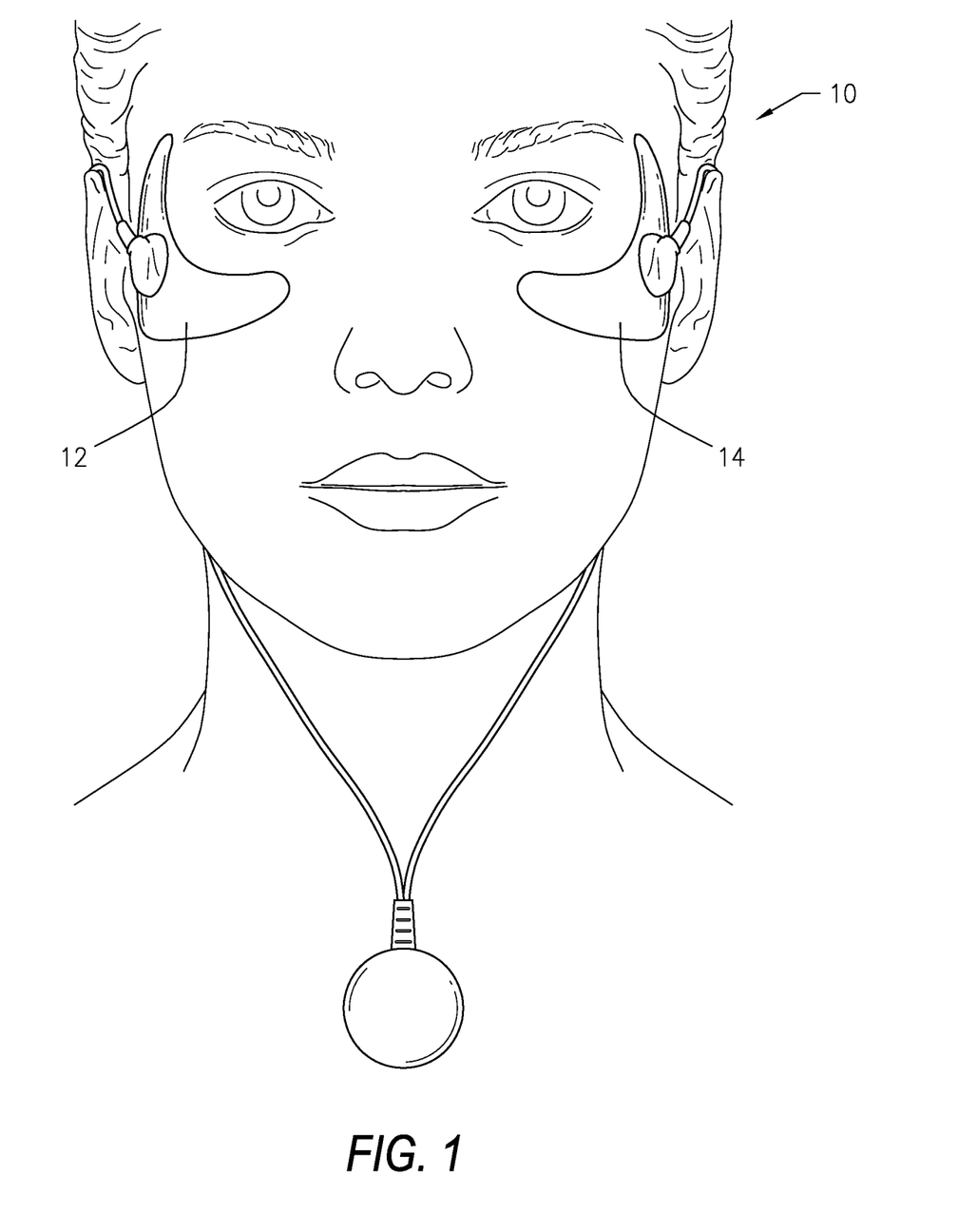
FIG. 1 is an illustration of a first preferred embodiment of a process and system for iontophoretic wrinkle reduction in accordance with the present invention.

Referring to the drawings in detail, FIG. 1 is an illustration of the first preferred embodiment 10 of the present invention surrounding the eyes of a consumer. As will be described herein in detail, a pair of patch assemblies 12 and 14 are applied and adhesively secured to the skin of a consumer surrounding the eyes.

Figure 2A:
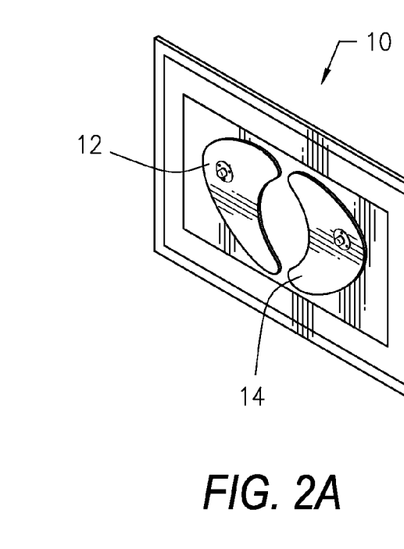
FIG. 2A illustrates a prospective view and FIG. 2B is an exploded view of patch assemblies of the first preferred embodiment of the present invention.
Figure 2B:
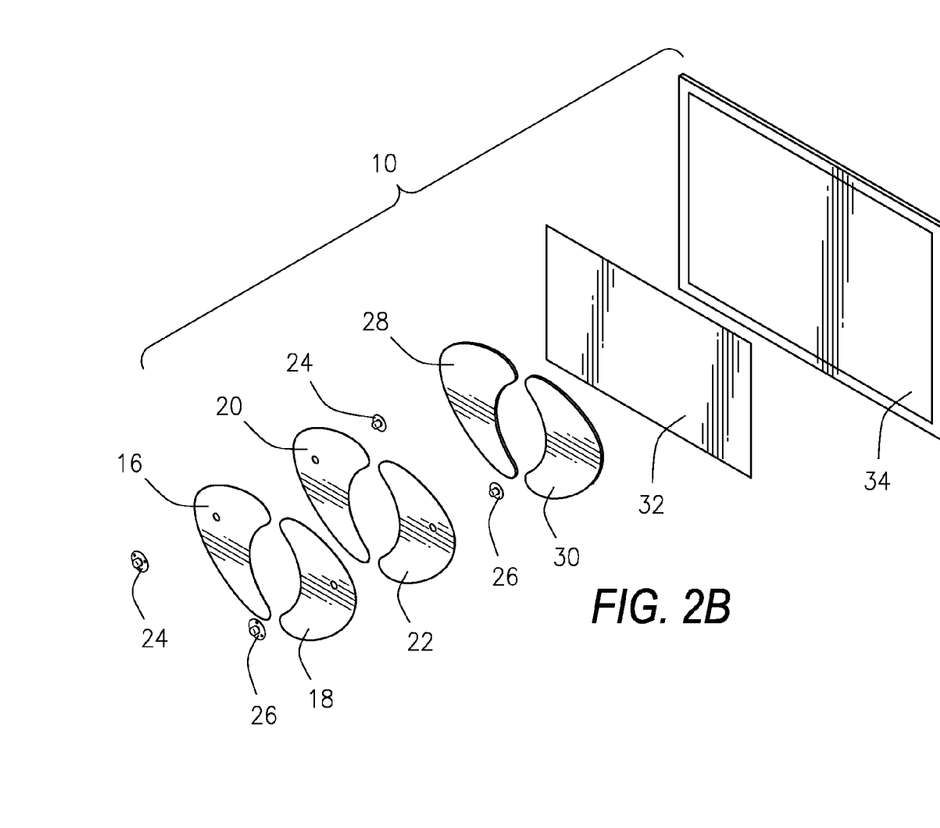

FIG. 2A illustrates a perspective view of the patch assemblies 12 and 14 prior to use and FIG. 2B is an exploded view of the patch assemblies 12 and 14 illustrating the components thereof.

Each of the patch assemblies 12 and 14 may include a substantially planar top sheet 16 and 18, respectively. The patch assemblies 12 and 14 may also include a substantially planar substrate 20 and 22, respectively.

The top sheet 16 and 18 and the substrates 20 and 22 each have holes or apertures which are aligned in order to receive conductive connectors or snaps 24 and 26 that pass therethrough. Each of the connectors or snaps may be in two-part form. In one non-limiting example, known type electro-mechanical connectors may be utilized.

Adjacent and on the substrates 20 and 22 are layers of a chemical composition, which may be in the nature of a hydrogel 28 and 30, respectively. The hydrogel 28 and 30 will contain active ingredients of the chemical composition and may also include an adhesive in order to adhere to the skin. The active ingredients may include hyaluronic acid, stressed yeast cell lysate, yeast cell derivative, and cross-linked synthetically derived protein. The hyaluronic acid may be in the range of 0.1 to 15%.

The hydrogel 28 and 30 are in fluid communication with the connections or snaps 24 and 26. Accordingly, current or voltage delivered to the connectors or snaps is delivered to the hydrogel. Alternatively or additionally, carbon ink may be added to the substrate layers to improve the conductivity of the electrode assembly.

The patch assemblies 12 and 14 may be stored and transported on a release liner sheet 32. The patch assemblies may be easily peeled off or removed from the liner sheet. The entire assemblies and the liner sheet 32 may be stored in a pouch 34.

Figure 3A:
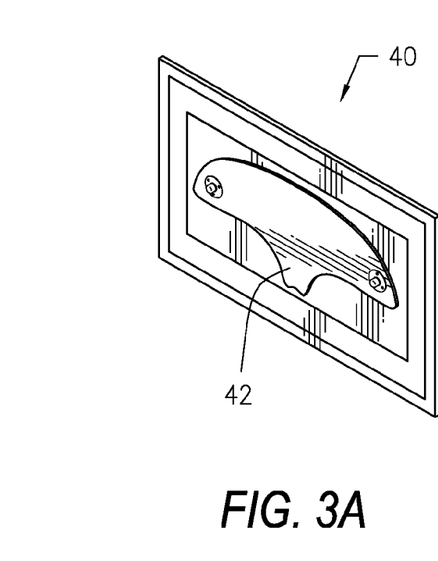
Figure 3B:
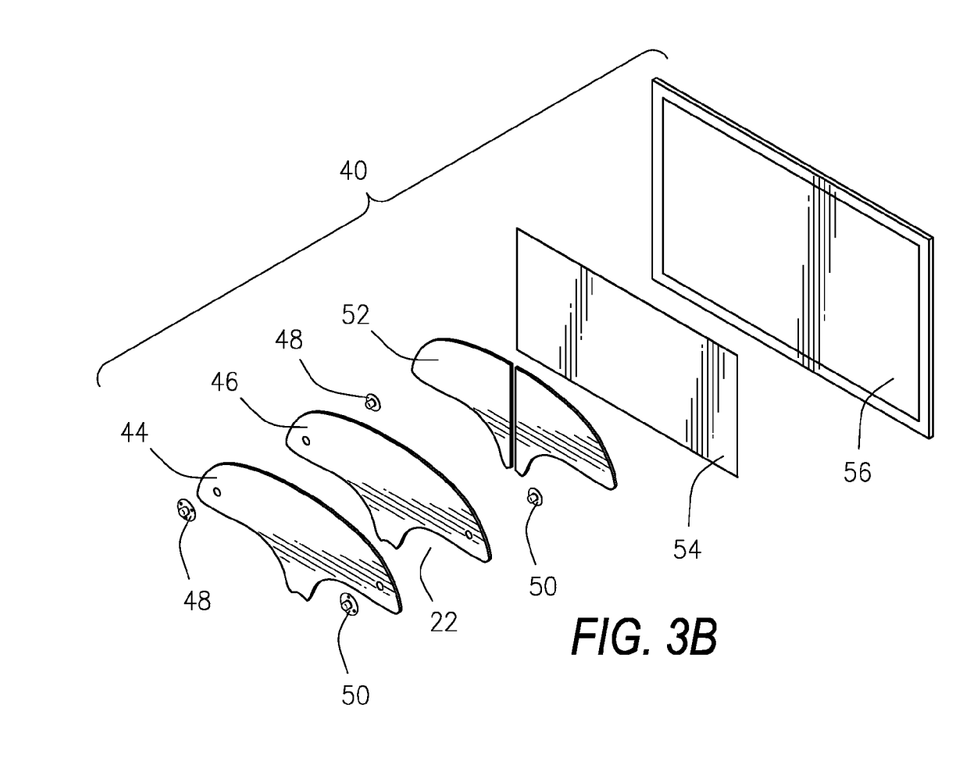
FIG. 3B is an exploded view of the patch assembly shown in FIG. 3A.

A second preferred embodiment of the present invention to be applied to the forehead and bridge of the nose is shown in assembled form in FIG. 3A and is shown exploded in FIG. 3B.

The second preferred embodiment includes a patch assembly 42 shown fully assembled in FIG. 3A prior to use. The patch assembly 42 may include a substantially planar top sheet 44 and an aligned substantially planar substrate 46. The top sheet 44 and substrate 46 each include aligned holes or apertures to receive a pair of connectors or snaps 48 and 50.

The patch assembly includes a layer of chemical composition in the hydrogel 52. The entire patch assembly 42 may be transported and stored on a liner sheet 54. The patch assembly 42 and the liner sheet may be stored in a pouch 56.

In a preferred arrangement, the patch assemblies are disposable after use. In each embodiment, the patch assemblies are connectable to an electronic locket assembly 60.

Figure 4:
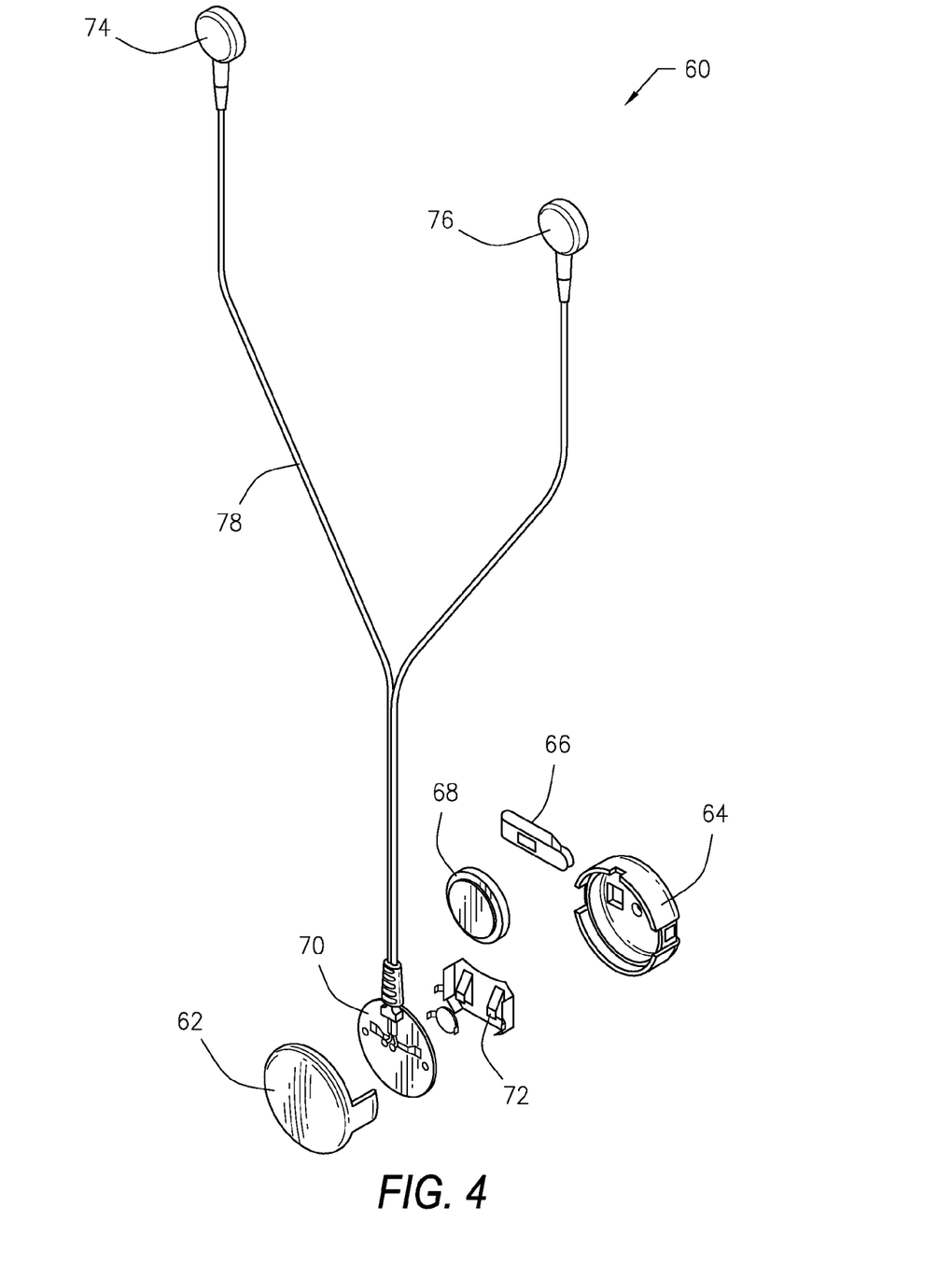
FIG. 4 illustrates an exploded view of an electronic locket assembly utilized in connection with the present invention.
Figures 5A, 5B:
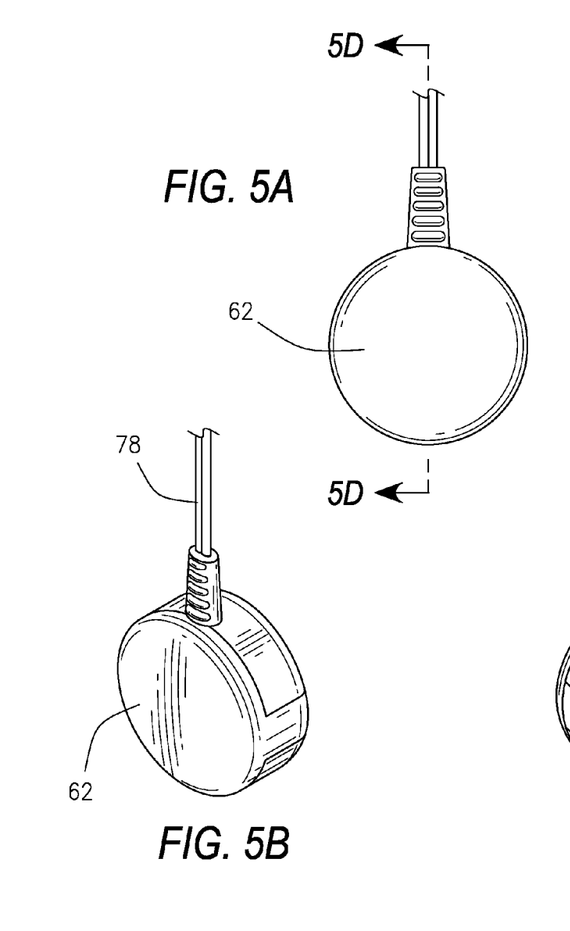
FIGS. 5A, 5B and 5C show alternate views of the lock assembly shown in FIG. 4.
Figures 5C, 5D:
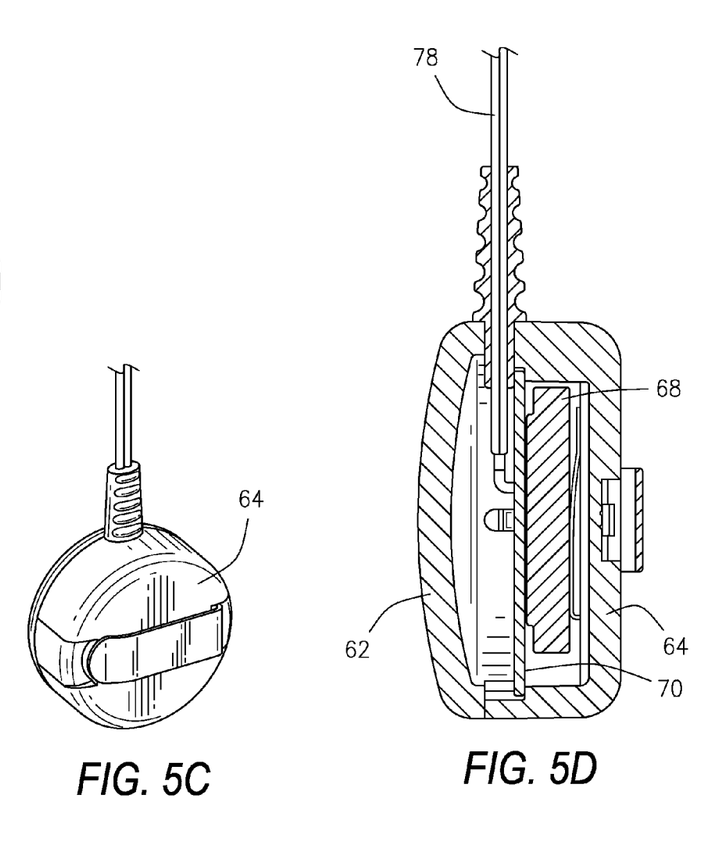
FIG. 5D is a sectional view taken through section line D-D of FIG. 5A.

FIG. 4 illustrates an exploded view of the electronic locket assembly 60. FIGS. 5A, 5B and 5C show alternate views of the locket assembly 60 with FIG. 51) illustrating a sectional view taken through section line D-D of FIG. 5A. The locket assembly 60 may include a front housing 62 which mates with a rear housing 64 to form an enclosure. Attached to the housing may be an optional clasp or clip 66. Within the enclosure of the housing is a battery 68 which powers a microprocessor based controller or printed circuit board (PCB) 70. A contact or contacts 72 connect the battery 68 to the controller 70.

The microprocessor based controller 70 is, in turn, wired to a pair of electrodes 74 and 76 through wires or a wiring harness 78.

The housing 62 and 64, the battery 68 and controller 70 may hang from or be suspended from the wiring harness 78.

The process and system of the present invention uses iontophoresis as the motive force for transdermal delivery of a defined amount of active ingredients.

In order to use the system of the present invention, initially, the patch assembly or assemblies are removed from the storage pouch and removed from the liner sheet and then positioned and aligned on the skin so that the chemical composition is in contact with and applied to the skin. The adhesive in the chemical composition serves to removably secure the patch assembly to the skin.

The pair of electrodes 74 and 76 are connected to the connectors or snaps of the patch assembly either in advance of application to the skin or after application. The process is continued by electronically activating the patch assembly.

Thereafter, a current is applied from the locket assembly 60 through the electrodes 74 and 76 into the chemical composition of the patch assembly for a selected time period. The active ingredients of the chemical composition are propelled into the skin of the consumer in order to relax the skin or achieve other beneficial results. After a selected period of time, the current is stopped and the patch assembly is removed from the skin. The patch assembly may be disconnected from the locket assembly 60. The patch assembly may thereafter be discarded.

As an additional step or measure, after the patch assembly is removed, any residue of the chemical composition may be massaged into the skin. The procedure may be periodically repeated.

Figure 6:
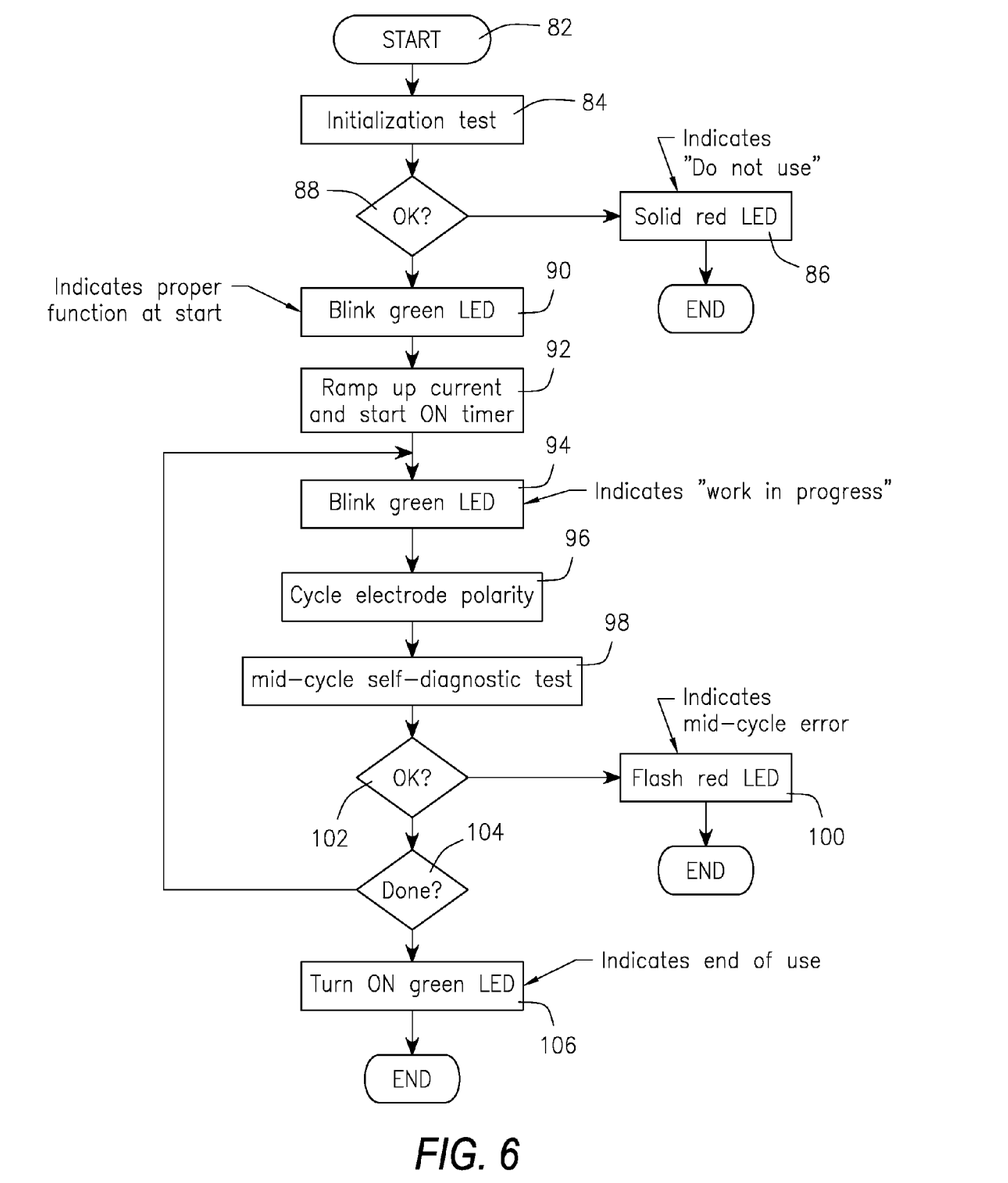
FIG. 6 is a diagrammatic flow chart of the process or method of application of the present invention.

FIG. 6 illustrates a diagrammatic flow chart of the process or method of application of the current during the delivery cycle of the invention. After start of the procedure, as shown in Box 82, the microprocessor based controller 70 will conduct a self initialization test as shown in Box 84. The process can be started conventionally by a button or switch or may be activated by a change in resistance between the electrodes triggered by skin contact.

If the initialization test does not result in an affirmative outcome, a solid red LED or other indicator will be provided as shown at Box 86 and the device will not be used. If the initialization test is satisfactory, as shown in Diamond 88, proper functioning will be indicated by a men LED as shown at Box 90.

Current to the device will be permitted to ramp up and a timer will be started as shown at Box 92. While the current is being delivered through the chemical composition and into the skin, a blinking green LED will be employed, as shown at Box 94.

Figure 7:
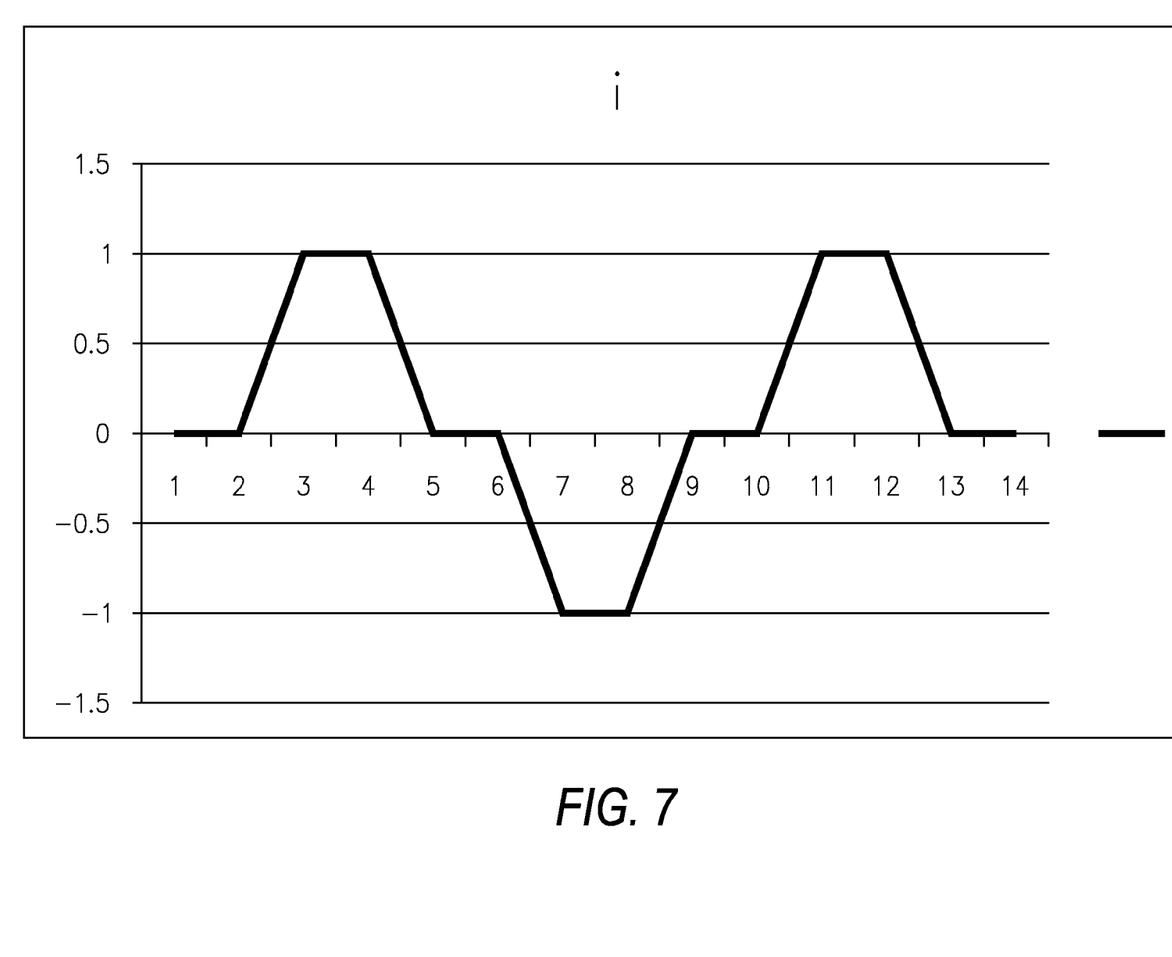
FIG. 7 illustrates a schematic representation of delivery of the electric current cycle during usage of the present invention.

The polarity of the current will be cycled or alternated as shown at Box 96. FIG. 7 illustrates a schematic representation of the current cycle. The current will be ramped up and then held for a time period. Thereafter, the current will be ramped down and the polarity changed.

Additionally, a mid-cycle self diagnostic test may be performed by the controller as shown at box 98. If an error is detected, a red LED will be displayed as shown at Box 100 and the procedure will be terminated. If the diagnostic test is satisfactory, as shown at Diamond 102, the procedure will be continued until the time period is completed as shown at Diamond 104. When the time period has been completed, the green light ceases to blink and remains on for a period of time to indicate the end of the procedure as shown at Box 106.

Thereafter, the patch assembly is removed from the skin and the locket assembly 60 is detached from the patch assembly. The locket assembly may be reused.

If at any time after the cycle has started, one of the electrodes or patch assemblies falls off, an error condition is signaled. If not reconnected within a reasonable time, the system defaults to an off position.

Whereas, the present invention has been described in relation to the drawings attached hereto, it should be understood that other and further modifications, apart from those shown or suggested herein, may be made within the spirit and scope of this invention.

What is claimed is:

1. A method of wrinkle and fine line reduction which comprises the steps of:
   positioning a first patch and a second patch to the skin of a consumer, the first patch and the second patch both comprising one or more active ingredients and an adhesive component;
   adhesively securing said first patch and said second patch to said skin of said consumer;
   controlling a first electrode and a second electrode with a powered microprocessor based controller connected to said first patch and said second patch, said first electrode connected to said first patch and said second electrode connected to said second patch;
   applying a current through said first and second electrodes in said patch for a selected time period, wherein applying a current comprises: (a) applying for a first time period a first current having a first polarity to the first electrode and a second current having a second polarity to the second electrode, the second current being equal in amplitude to the first current and the second polarity being opposite the first polarity; (b) reversing the polarity of each of said electrodes a first time such that the first and second electrodes are subjected to equal amplitude currents with opposite polarities during a second time period; and (c) reversing the polarity of said electrodes a second time such that the first and second electrodes are subjected to equal amplitude currents with opposite polarities during a third time period, wherein applying a current results in propelling said active ingredients stored in said patch into said skin of said consumer through said current in order to affect said skin of said consumer; and
   removing said patch after said selected time period.

2. The method of wrinkle and fine line reduction as set forth in claim 1 including the additional steps after said removing said patch of:
   massaging any residue of said active ingredients into said skin, and repeating one or more of the positioning, adhesively securing, controlling, or applying foregoing steps.

3. The method of wrinkle and fine line reduction as set forth in claim 1 wherein at least one of said active ingredients comprise hyaluronic acid.

4. The A method of wrinkle and fine line reduction as set forth in claim 1 wherein said step of applying a current through said first and second electrodes in said patch includes: ramping up the current with an initial polarity until the first current is reached.

5. The method of wrinkle and fine line reduction as set forth in claim 1 further comprising the step of controlling application of current by programming a microprocessor.

6. The method of wrinkle and fine line reduction as set forth in claim 1 further comprising powering a light in said controller during said application of said current through said electrodes.

7. The method of wrinkle and fine line reduction as set forth in claim 2 further comprising applying a dermal filler to said skin in between said repeating of said positioning, adhesively securing, controlling, or applying steps.

8. The method of wrinkle and fine line reduction as set forth in claim 1 wherein said selected time period is monitored by a timer which is activated by contact of said patch with said skin.

9. The method of wrinkle and fine line reduction as set forth in claim 1 wherein said selected time period for said application of current is approximately thirty minutes.

10. The method of wrinkle and fine line reduction as set forth in claim 1 wherein said patch is disposable.

11. The method of wrinkle and fine line reduction as set forth in claim 1 wherein said controller is reusable.

12. A wrinkle and fine line reduction apparatus, which comprises:
   a disposable patch for positioning and aligning on skin of a consumer;
   a chemical composition on one side of said patch, said chemical composition including one or more active ingredients and an adhesive component;
   a pair of electrodes operably connected to a powered microprocessor based controller connected to said patch, said controller configured to control a current through said electrodes, said controller configured to reverse the polarity of each of said electrodes a plurality of times such that the electrodes are each subject to equal and opposite polarities with respect to each other; and
   a power source to generate the current through said electrodes to propel said active ingredients into said skin of said patient in order to affect said skin of said consumer.

13. The wrinkle and fine line reduction apparatus as set forth in claim 12 wherein at least one of said active ingredients comprises hyaluronic acid.

14. The wrinkle and fine line reduction apparatus as set forth in claim 12 further comprising a timer to generate a current for a selected period of time.

* * * * *

UNITED STATES PATENT AND TRADEMARK OFFICE
CERTIFICATE OF CORRECTION

| | | |
|---|---|---|
| PATENT NO. | : 8,747,383 B2 | Page 1 of 1 |
| APPLICATION NO. | : 12/970224 | |
| DATED | : June 10, 2014 | |
| INVENTOR(S) | : Ray Francis | |

It is certified that error appears in the above-identified patent and that said Letters Patent is hereby corrected as shown below:

In the Specification:

In column 1 at line 15, Change "line" to --fine--.

In column 1 at line 32, Change "line" to --fine--.

In column 4 at line 38, Change "invention," to --invention--.

In column 4 at line 60, Change "removed," to --removed--.

In column 5 at line 8, Change "men" to --green--.

In the Claims:

In column 6 at line 13, In Claim 2, after "applying" delete "foregoing".

In column 6 at line 17, In Claim 4, change "The A" to --The--.

Signed and Sealed this
Twenty-first Day of April, 2015

Michelle K. Lee
*Director of the United States Patent and Trademark Office*